| United States Patent [19] | [11] | 4,374,979 |
|---|---|---|
| Mitscher | [45] | Feb. 22, 1983 |

[54] REGIOSPECIFIC SYNTHESIS OF ANTHRACYCLINONE COMPOUNDS SUCH AS DAUNOMYCINONE

[75] Inventor: Lester A. Mitscher, Lawrence, Kans.

[73] Assignee: The University of Kansas Endowment Association, Lawrence, Kans.

[21] Appl. No.: 258,193

[22] Filed: Apr. 27, 1981

[51] Int. Cl.$^3$ ............... C07H 15/24; C07C 49/72; C07C 49/74; C07C 49/84
[52] U.S. Cl. ............... 536/6.4; 260/383; 260/365; 260/351.1; 260/351.5
[58] Field of Search ............ 260/383, 365, 351.5, 260/351.1, 694; 568/347, 348; 536/17 A

[56] References Cited

U.S. PATENT DOCUMENTS

| 3,590,028 | 6/1971 | Arcamone et al. | 536/17 A |
|---|---|---|---|
| 4,070,382 | 1/1978 | Kende et al. | 260/365 |
| 4,132,721 | 1/1979 | Bernardi et al. | 260/365 |
| 4,244,880 | 1/1981 | Alexander et al. | 260/365 |

OTHER PUBLICATIONS

Kelly and Tsang, "The Synthesis of 4-Demethoxydaunomycin" Tetrahedron Letter, No. 46, 1978, pp. 4457-4460.
Braun, "Regioselektive Synthese Von Daunomycinon und-γ-Rhodomycinon", Tetrahedron Letters, vol. 21, 1980, pp. 3871-3874.
Reynolds et al., "A Regiospecific Synthesis of Anthracyclinones", Tetrahedron Letters, No. 28, 1977, pp. 2383-2386.
Alexander and Mitscher, "A Short, Efficient Synthesis of an Anthracycline Antitumor Antibiotic Synthon," Tetrahedron Letters, No. 37, 1978, pp. 3403-3406.
Barfknecht et al., "Potential Psychotomimetics 2-Amino-1,2,3,4-tetahydronaphthalene Analogs", Journal of Medicinal Chemistry, vol. 16, No. 7, 1973, pp. 804-808.
Yee and Schultz, "Carbonyl Transposition Studies", Journal of Organic Chemistry, vol. 44, No. 5, 1979, pp. 719-724.
Acton et al., "Total Synthesis of the Antitumor Antibiotic Danoubien Coupling of the Sugar and Aglycone, Journal of Medicinal Chemistry, vol. 17, No. 6, 1974, pp. 659-660.
Lee et al., "Daunomycinone Analogues via the Diels-Alder Reaction", Journal of Organic Chemistry, vol. 41, No. 13, 1976, pp. 2297-2302.
Swenton and Reynolds, "A Regiospecific Synthesis of the Anthracycline Aglycones, Daunomycinone and Adriamycinone", Journal of the American Chemical Society, vol. 100, No. 19, 1978, pp. 6188-6195.
Parker and Kallmerten, "Efficient, Regiospecific Synthesis of Anthracycline Intermediates, Total Synthesis of Daunomycin", Journal of the American Chemical Society, vol. 102, 1980, pp. 5881-5886.
Kende et al., "A Regiospecific Total Synthesis of (±) Daunomycinone", Tetrahedron Letters, No. 14, 1979, pp. 1201-1204.
Arcamone et al., "Stereocontrolled Glycosidation of Daunomycinone", Journal of Medicinal Chemistry, vol. 19, No. 5, 1976, pp. 733-734.

*Primary Examiner*—Charles F. Warren
*Assistant Examiner*—Raymond Covington
*Attorney, Agent, or Firm*—Biebel, French & Nauman

[57] ABSTRACT

A regiospecific synthesis for anthracyclinones asymmetric is disclosed. The synthesis is based upon a regiospecific bromination of the C-7 position of the α-tetralone which after transposing the keto group to the β-position and reaction with an organo-lithium compound is condensed with a phthalate ester.

10 Claims, No Drawings

REGIOSPECIFIC SYNTHESIS OF ANTHRACYCLINONE COMPOUNDS SUCH AS DAUNOMYCINONE

BACKGROUND OF THE INVENTION

The present invention relates to the synthesis of anthracycline compounds and particularly compounds such as daunomycinone which are constituents of anticancer antibiotics such as doxorubicin and daunorubicin.

Anthracycline antibiotics have been found effective in treating a wide variety of cancers including acute myeloblastic and lymphoblastic leukemia and as a result their synthesis has attracted considerable attention. These antibiotics occur as glycosides formed of a tetracyclic aglycone (anthracyclinone) and a 3-amino-2,3,6 trideoxy sugar and can be represented by the formula (I):

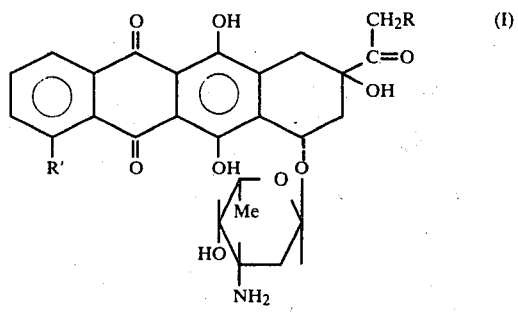

In this formula use of the following constituent groups leads to the compounds as listed:

| R = H | R' = OCH$_3$ | Daunorubicin |
|---|---|---|
| R = OH | R' = OCH$_3$ | Doxorubicin |
| R = OH | R' = OH | Carminomycin |

The antibiotic doxorubicin is the subject of U.S. Pat. No. 3,590,028 and is available as the hydrochloride under the label "Adriamycin" ™ from Adria Laboratories, Inc., Dublin, Ohio. Adriamycin has been used successfully to produce regression in several carcinoma and disseminated neoplastic conditions and is a prescribed antineoplast.

Conventionally, anthracycline antibiotics are produced by aerobic fermentation of strains of *Streptomyces*. However, fermentations are inherently restricted in terms of the amounts of antibiotic they yield, the nature of the antibiotics produced and the conditions and apparatus under which they can be successfully conducted. Fermentations are also incapable of yielding analogues. Thus there is a need for more versatile synthesis of these compounds. More particularly there is a need for syntheses able to yield derivatives of these compounds which may be more effective than the natural substances. Accordingly, efforts have been directed to developing effective and flexible synthetic routes to these tetracycline type antibiotics.

One synthesis which has been treated somewhat extensively in the literature provides the antibiotics in good yields by coupling the separately prepared aglycone and amino sugar. Under this approach daunorubicin and doxorubicin have been prepared by glycosidation of daunomycinone and adriamycinone, respectively, with daunosamine derivatives. Using this process the major constituents of the antibiotics are separately synthesized and it is possible to individually modify the structure of the aglycone and amino sugar and thereby obtain access to a variety of antibiotic derivatives. The present invention has for its object synthesis of the anthracyclinone moiety of these antibiotics.

While the aglycones constituting these antibiotics have been artificially synthesized before, the synthetic routes used have not been satisfactory. They have been particularly unsuitable for manufacturing the asymmetric aglycones such as daunomycinone because it has only been possible to obtain the regioselectivity that is required by adding numerous steps to the synthesis.

Alexander and Mitscher, *Tetrahedron Letters*, 3043 (1978), disclose a convenient synthesis of symmetrical anthracyclines from a decalin embodying major elements of two rings of the final antibiotic and coupled this through an organometallic reagent with a phthalic ester to provide the remaining rings of the quinone system. This product was further elaborated by well-established means. The reaction is shown in Equation I below and it will be noted that it is similar to the present invention in that the synthesis relies upon a bromination and subsequent conjugation of the bromide with a phthalic ester.

Equation I

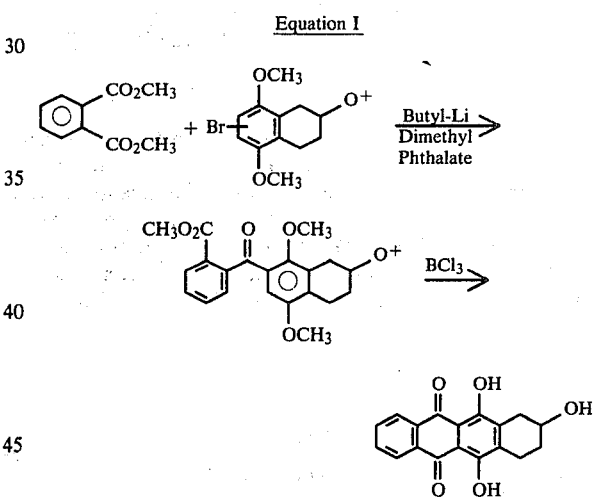

The principal utility of this synthesis is limited to preparation of analogues symmetrical about the D-ring, because the bromination of the decalin is not specific. Only when used to synthesize symmetric products does the use of a mixture of bromide regioisomers not affect the yield.

Braun, *Tetrahedron Letters*, 21, 3871 (1980), addresses the regioselectivity problem by using an aliphatic moiety to direct bromination. [Braun is mentioned because it is another approach to regioselectivity. Its inclusion here is not intended as an admission of prior art.] The synthesis proceeds via formation of a 7-bromo,5,8-dimethoxy-α-tetralone which conjugates with phthalic anhydride yielding a product ultimately used in a ring closure via an organometallic reagent. The synthesis is outlined in Equation II.

Equation II

-continued
Equation II

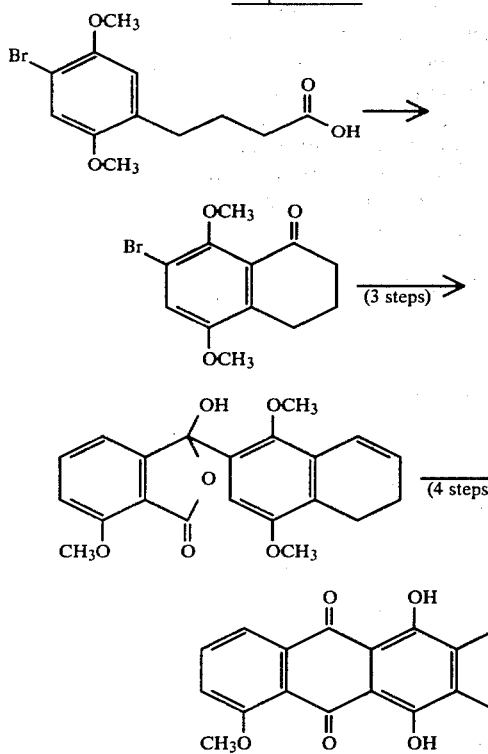

Swenton et al, *J. Am. Chem. Soc.*, 100, 6188 (1978) have devised a regiospecific method for synthesizing 7,9-dideoxydaunomycinone in which the key steps involve bromination of 2-hydroxy-5-methoxybenzaldehyde which is further elaborated and then condensed with dimethyl 3-methoxyphthalate to achieve a regiospecific bond formation as shown in Equation III below:

Equation III

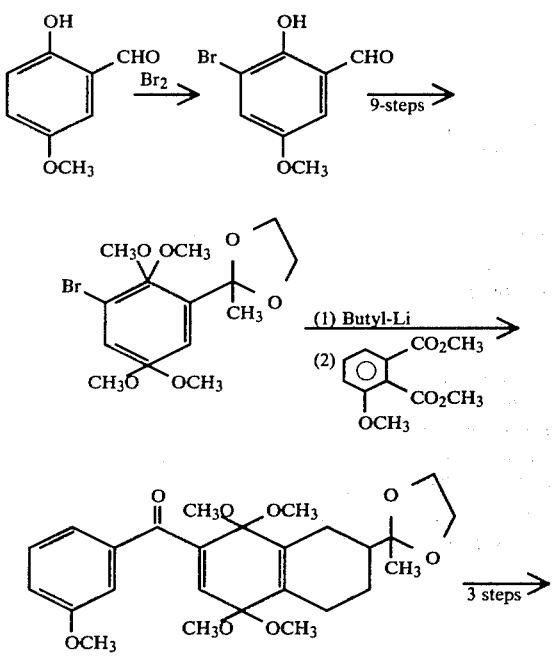

-continued
Equation III

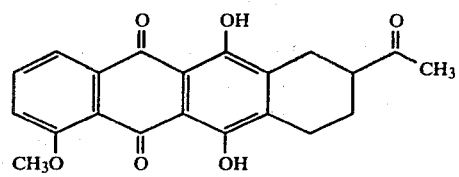

In a much longer sequence, Parker and Kallmerten, *J. Am. Chem. Soc.* 102, 5881 (1980), synthesized 7,9-dideoxydaunomycinone. The final product is a 7,9,didesoxyanthracycline. The synthesis proceeds via a cyano decalin and the key step is the conjugate addition shown in Equation IV below:

Eq. IV.

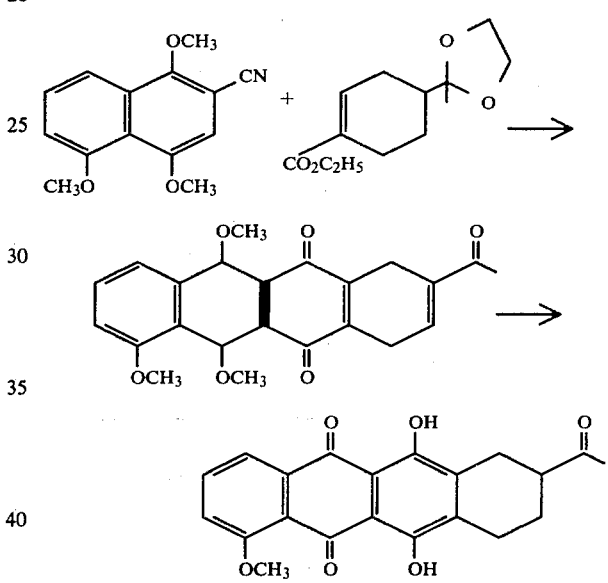

Kende, *Tetrahedron Letters*, 1201 (1979) has developed a similar synthesis, and as with most of these processes regioselectivity is obtained only by adding numerous steps to the process.

The above processes are generally unsuitable for synthesizing the asymmetric anthracycline compounds because regioselectivity is only achieved at the expense of adding numerous steps to the reaction sequence. This limits flexibility in producing analogues and increases the economic investment in each intermediate. They are also not suitable for large scale operations. Accordingly, there is a need for an anthracycline synthesis involving fewer steps, which is amenable to the production of analogues and which can be carried out effectively on a large scale. There is also a need for a synthesis which is able to yield anthracycline derivatives such as daunomycinone which are assymetric about the D-ring.

SUMMARY OF THE INVENTION

In accordance with the pressent invention, anthracycline compounds are produced by a regiospecific synthesis characterized in its principal embodiment by bromination of the 7-position of the α-tetralone, 3,4-dihydro-5,8,dimethoxy-1 (2H) naphthalone, and condensation of 7-bromo-5,8-dimethoxy-α-tetralone with a 3-methoxy phthalate ester. In previous applications and particularly those of Alexander & Mitscher, a way has not been found to produce the 7-bromo-α-tetralone in a regiospecific manner. A mixture of bromo compounds substituted at the 6- and 7-positions results. As a result the previous processes are only suitable for making compounds which are symmetrical about the aromatic rings.

The process of the present invention is described in more detail below by reference to the following reaction sequence for the synthesis of daunomycinone wherein the starting materials and intermediates are identified by reference to the compounds as numbered:

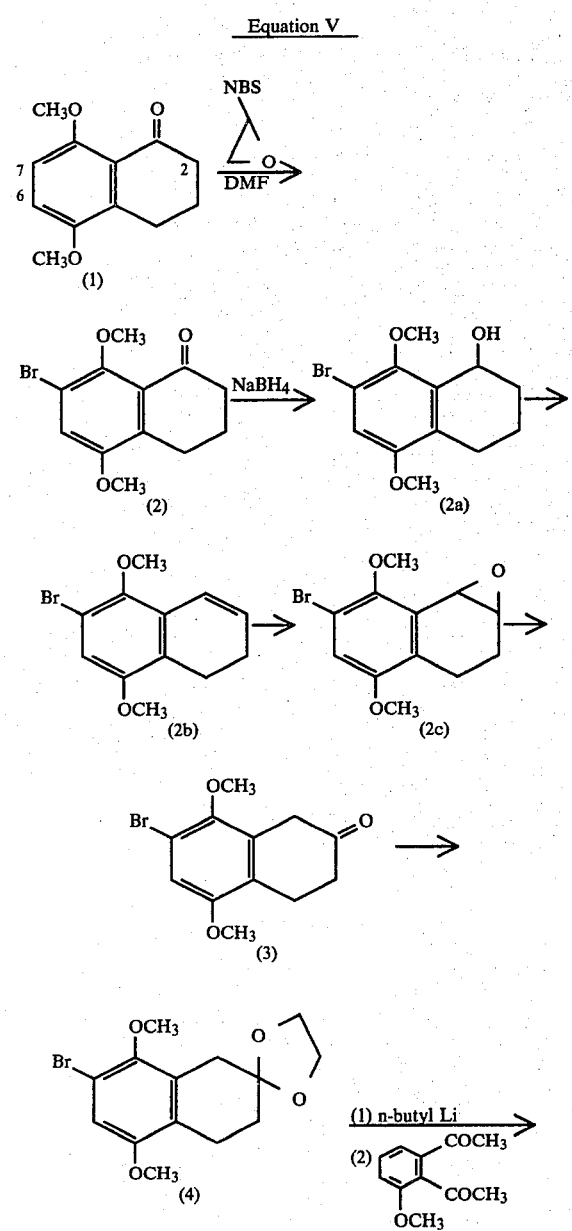

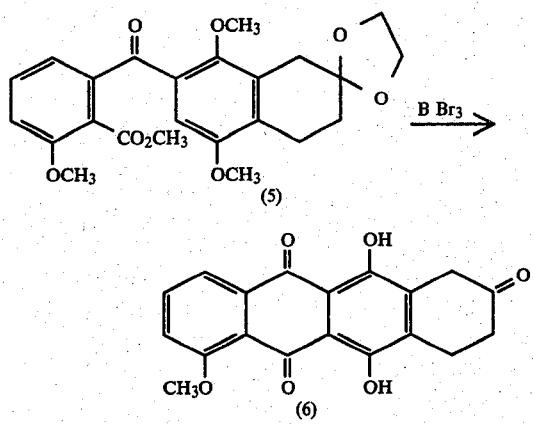

DETAILED DESCRIPTION OF THE INVENTION

The present invention presents a short regiospecific route to daunomycinone and related anthracyclinone compounds. This route relies upon a regiospecific bromination of a tetralone yielding the 7-bromo derivative (2).

The starting material (1) can be prepared by known procedures such as that described by Barfknecht et al *J. Med. Chem.* 16, 804 (1973). 5,8-dimethoxy-α-tetralone is prepared from 1,4-dimethoxy benzene by Friedel-Crafts reaction with 3-carbomethoxy propionyl chloride, followed by reduction of the ketone moiety and ring closure. Other routes are available. For example, compound (1) has also been made in one step by Friedel-Craftsreaction of benzene and α-butyrolactone. (See Olson et al, *Org. Syn. Call.* 4, 898 (1963). The former procedure is preferred for its overall yields although it involves more steps.

To synthesize asymmetric anthracylinones directly in a few reaction steps in accordance with the present invention, Compound (2) cannot be a mixture of monobrominated compounds, but must be the single isomer having bromine present at the 7-position. Two undesirable brominations are avoided in the synthesis of Compound (2) in accordance with the present invention. The first is substitution of the 6-position which was the drawback of the Alexander process. 6-Position bromination is avoided in the present invention as a result of the directing effects of the o-methoxy group, the m-keto group and the p-alkyl group (with respect to the 7-position) in Compound (1). These groups uniquely activate the 7-position over the 6-position.

The second substitution to be avoided is of the methylene group at the 2-position of the α-tetralone (1). Bromination of (1) to yield specifically the 7-bromo derivative presents unique problems due to the possibility of electrophilic substitution at the methylene group. Attempts to produce the 7-bromo derivative by a swamping catalyst technique using excess aluminum chloride to deactivate the aliphatic side chains proved unsuccessful and resulted in a mixture of products. A considerable amount of side chain bromination was also encountered using bromine in aqueous acetic acid. Attempts with bromine in chloroform or carbon tetrachloride in the presence of HBr scavengers such as acetamide or propylene oxide resulted in a mixture of starting material and side-chain brominated compound.

To be effective bromination of compound (1) should yield the 7-bromo compound in a preponderant ratio as compared to other isomers. As a result of further experimentation and investigation it was found that it is necessary to completely suppress enolization of the ketone or bromination would occur at the 2-position in preference to the 7-position. It was also found that an N-bromosuccinimide-dimethylformamide system yields the 7-bromo derivative with only minor amounts of 2-substitution. Further investigation lead to the discovery that when this reaction is carried out in the presence of an HBr scavenger such as propylene oxide, the 7-bromo derivative exclusively is produced. Thus in accordance with a preferred embodiment of the present invention, 7-bromo-5,8-dimethoxy α-tetralone (2) is produced by reacting the 5,8-dimethoxy α-tetralone (1) in an N-bromosuccinimide-dimethylformamide system in the presence of propylene oxide. Typically this reaction is carried out at moderate to low temperatures to ensure selectivity, with a range of 4° to 25° C. being the preferred embodiment effecting a compromise between regioselectivity and a suitable reaction rate. At least one molar equivalent of halogenating agent is employed— preferably a small molar excess is used. Any reaction inert solvent is satisfactory, however, dimethylformamide has been found to be particularly convenient. Other active brominating agents, such as for example, N-bromoacetamide, and the like will be recognized by those skilled in the art as essentially equivalent to N-bromosuccinimide for the purpose at hand.

In this system, propylene oxide can be replaced by other HBr scavengers such as diisopropylethylamine and dissopropylethylamine proton sponge (Aldrich Chemical Co.), although propylene oxide is generally preferred.

The conversion of compound (2) to compound (3) involves transposition of the keto group from the 1 to the 2-position. Transposition of the keto groups can be accomplished using a variety of classical methods and the practictioner need not limit himself to the methods shown here. Fristad et al, *J. Org. Chem.*, 44, 4733 (1979) and the references cited therein and Yee et al, *J. Org. Chem.*, 44, 719 (1979) and the references cited therein disclose other schemes. The technique shown in Equation V is preferred for its simplicity and because the reagents are inexpensive and this sequence can be carried out on a large scale.

The Compound (2) is reduced to its alcohol (2A) which is effectively dehydrated to afford the compound (2B) having an olefinic functionality. Normally hydroboration would be expected to add back the hydroxy group at the β position thereby yielding the 2-keto compound upon subsequent oxidation, however, attempts at this reaction sequence using BH$_3$-THF and 9-borabicyclo-[3.3.1]-nonane resulted in the α-hydroxy compound and not the β-hydroxy compound that was desired. Accordingly, the olefin (2B) was epoxidized to the compound (2C) and treated with trifluoro acetic acid to yield Compound (3) with the keto group at the 2-position. These reactions are carried out under conditions generally employed in the art and will typically yield compound (3) in an overall yield of 30 to 60% based on compound (2).

More specifically, reduction of the keto group of Compound 2 to the hydroxy can be accomplished using a variety of reducing agents such as sodium borohydride, other metal hydrides, catalytic hydrogenation and the like. Sodium borohydride is preferred. It is most convenient to carry this reaction out in alcohol and other reaction inert solvents at room temperature to 60° C. Alcohol (2A) need not be isolated but can be dehydrated in the same reaction flask.

The 1-hydroxy compound (2A) can be effectively dehydrated using a strong acid such as hydrochloric acid, tosic acid, and the like, and heating to 80° to 90° C. to accelerate the reaction. The olefin (2B) which results does not seem able to add back the hydroxy group at the β-position using typical methods. Therefore, in accordance with this scheme it is epoxidized to yield Compound (2C). This reaction is carried out in a conventional manner using a peroxybenzoic acid.

The epoxide (2C) readily converts to Compound (3) upon reacting with trifluoroacetic acid which opens the epoxide ring and yields the transposed keto group. While initial experiences with HCl and acetic acid did not yield the keto group at the 2-position in acceptable yield in some cases, it is expected that under selected conditions these and other acids in addition to trifluoroacetic acid will react to yield Compound (3).

Compound (3) is very flexible from the standpoint of making analogues. In copending application Ser. No. 257,832 filed on even date herewith, Mitscher et al disclose that studies on the metabolic inactivation of daunomycin and doxorubicin indicate that gem dimethyl group at the 10 position may protect the antibiotic analogue from metabolic inactivation. One of the major routes whereby these compounds are metabolized being reduction of the carbonyl group at position 13. Evidence that the gem dimethyl group provides resistance to enzymatic inactivation is based in part upon an inability to ketalize the side chain of this ketone. These 10,10-derivatives can be prepared by reacting Compound (3) with methyl iodide in the presence of sodium hydride. This results in a dimethyl addition to compound (3) at the 1-position. Subsequent reaction in accordance with the present invention yields, for example 10,10-dimethyl doxorubicin. The gem group assists the synthesis by preventing aromatization of the A-ring. It is envisioned that other lower alkyl and aryl groups and other moderately bulky blocking groups (which are inert to the subsequent necessary chemical manipulations) may also be employed to achieve this result.

Other compounds that can be prepared are illustrated below. Compound II A is prepared by reacting the 2-keto group in Compound (3) with the lithium salt of methyl vinyl ether. Compound II A may be used directly or followed by acid-treatment to deblock, and then treatment with ethylene glycol and an acid to yield Compound II B. Other reaction sequences (such as the addition of a metalloacetylene moiety followed by mercury salt, hydration and blocking and the like) can also be used to yield a suitably protected hydroxy acetyl side chain. This can also be used to protect the keto group during the subsequent synthetic steps.

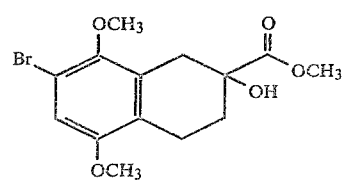

-continued

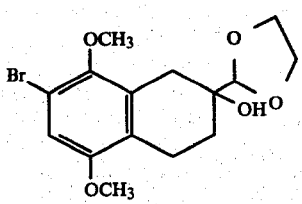

II B

To continue the synthesis, the keto group at the 2-position in Compound (3) is protected. Various techniques can be used for this purpose as discussed above. In the synthesis illustrated in the introduction, the keto group is protected as the dioxolane, Compound (4).

For conjugation with the phthalate, compound 4 is successively lithiated and reacted with the phthalate. The reactions are preferably carried out in the same flask or reactor and without interruption. The reactions must be conducted under absolutely dry conditions.

Those skilled in the art will recognize that in addition to reacting with lithium n-butylate lithiation may be accomplished by reacting with other lithium compounds. Furthermore, it may be possible to react other metallic derivatives of Compound (4) with the phthalate to yield the conjugate Compound (5). For example, reactions are envisioned using the Grignard derivatives. This reaction is preferably carried out in THF but other reaction inert solvents may also be used.

The lithiated compound is reacted with a phthalate ester to produce the conjugate (5). In the reactions illustrated, daunomycinone is the target and, therefore, the 3-methoxy phthalate is reacted. The phthalate is preferably reacted as the methyl or the ethyl ester. Reaction with the phthalate is accomplished by adding the desired phthalate ester slowly to the preformed lithiated Compound 4 in an inert gaseous atmosphere at a low temperature (−80° C. is satisfactory) and then allowing the mixture to warm up slowly to room temperature. Preferential reaction is obtained at the least hindered carbolkoxy group of the phthalate. Given the asymmetry of the organometallic reagent derived from Compound 4, other phthalate esters can profitably be employed (e.g., the 3,4-dimethoxy, 3,4-methylenedioxy, 3,5-dimethoxy, 3-methyl, etc. phthalates), in order to produce by further elaboration a wide variety of synthetic analogues to doxorubicin and daunorubicin.

Preliminary attempts to cyclize the conjugate to yield the anthraquinone using boron trifluoride and trifluoride methylene chloride were unsuccessful in the laboratory, but a more conventional procedure by trifluoromethanesulfonic acid yielded the anthraquinone. It is anticipated that a variety of cyclodehydrating procedures (such as, but not limited to, polyphosphoric acid, sulfuric acid, and the like) will effect this cyclization upon proper choice of reaction conditions following routine laboratory experimentation. Compound 6 as produced in the present invention, is a well-known anthracyclinone intermediate having previously been elaborated to daunomycinone and thence to daunorubicin and doxorubicin in an actual or a formal sense in many anthracycline syntheses. See, for example, U.S. Pat. No. 4,244,880.

The synthesis of the present invention has been explained by reference to the synthesis of daunomycinone. The synthesis can, however, be modified to yield other anthracyclinones. In particular, the intermediate β-tetralone (Compound (3)) and the phthalate ester may be modified to yield other rotationally unsymmetrical analogues. Modifications of Compound 3 have already been discussed. By substituting the β-tetralone, substituents can be introduced on the A-ring of the anthracyclinone.

The present invention can also be used to synthesize rhodomycinone or carminomycinone (compounds in which the methoxy group on the D-ring in daunomycinone is replaced by a hydroxyl group) by use of an appropriate phthalate ester whose blocking group can be removed by appropriate choice of reagents and reaction conditions so that the final antibiotic bears a free phenolic OH group at the C-4 position.

Similarly the aglycone moiety of doxorubicin may be prepared in accordance with the present invention by introducing the 14-OH group at an appropriate stage in the synthesis.

Aglycones or anthracyclinones prepared in accordance with the present invention are coupled with amino sugars to yield useful anticancer antibiotics in a conventional manner. Suitable reactions are disclosed by Acton, et al, *J. Med. Chem.*, 17, 659 (1974); Smith et al, *J. Am. Chem. Soc.* 98, 1969 (1976) and *J. Org. Chem.*, 42, (1977) and Acramone et al, *J. Med. Chem.*, 19, 733 (1976) among others. The principal amino sugars with which anthracyclinones produced in accordance with the present invention may be coupled to yield useful antibiotics include daunosamine, 4'-epidaunosamine and 4'-deoxydaunosamine.

Although a relatively simple chemical and widely applicable in anthracycline synthesis, dimethyl 3-methoxy-phthalate is not commercially available. A number of syntheses are reported but proceed in low yields, from difficult to obtain starting materials or are lengthy. A preferred synthesis was found to be nucleophilic aromatic displacement of the nitro group in 3-nitrophthalic anhydride. Refluxing in methanol in the presence of $H_2SO_4$ yields dimethyl 3-nitrophthalate, which is smoothly converted to 2-carbomethoxy-3-methoxybenzoic acid by stirring at room temperature with sodium methoxide in hexamethylphosphoric triamide for two days. The intermediate diester easily undergoes partial saponification during aqueous work-up to yield the acylomonester which has been shown to have the free acid in a position meta to the methoxy group. A small amount of the desired diester remains unhydrolized and can be recovered from the basic reaction mixture by extracting with benzene. The synthesis of the diester is completed by quantitative reaction of the monoester with diazomethane in ether/methanol. A preferred synthesis is illustrated by the following preparation example but the practitioner will recognize other routes to this compound.

PREPARATION EXAMPLE

A. Dimethyl 3-nitrophthalate

Commercial 3-nitro phthalic anhydride (10.0 g) was dissolved in 100 ml of 5% fuming sulfuric acid in methanol solution and this was refluxed overnight. The solution was cooled and poured into 150 ml of aqueous methanol, whereupon 7.5 g of dimethyl 3-nitrophthalate separated as colorless needles, mp 68°–69° C. The mother liquor was concentrated and neutralized with saturated sodium bicarbonate solution and extracted with ethyl acetate. Evaporation gave an additional 2.5 g (total 10.0 g, 81% yield) of essentially pure product. $^1$H NMR (CDCl$_3$) δ 3.96 (3H, s, ArCOOC$\underline{H}_3$), 4.03 (3H, s, ArCOOCH₃), the aromatic protons exhibited an AB₂ pattern, the A part centered at 7.70 (1H, t, J=8 Hz) and the B part centered at 8.40 (2H, d, J=8 Hz); IR (KBr) 1745, 1730, 1610, 1570, 810 cm$^{-1}$ etc.; mass spectrum m/e (rel. intensity) 239 (M+, 3%), 209 M+-2CH₃, 100%), 208 (M+-OHC₃), etc.

Anal. for $C_{10}H_9NO_6$: Calcd: C, 50.21; H, 3.79; N, 5.85. Found: C, 49.90; H, 3.85, N, 5.55.

B. 2-Carbomethoxy-3-Methoxybenzoic Acid

Dimethyl 3-nitrophthalate (4.8 g, 20 mmol) was added to a cold solution of sodium methoxide (2.61 g, 48.3 mmol) in dry hexamethylphosphoric triamide (75 ml). The resulting dark solution was gradually brought to room temperature and the reaction mixture was stirred for 44 hrs. It was then diluted with water (125 ml) and extracted with benzene. (This extract contained a variable quantity of dimethyl 3-methoxyphthalate. The aqueous layer was acidified with hydrochloric acid and extracted with benzene. The combined organic layers were washed with water (5×30 ml) and then brine (1×15 ml), dried over sodium sulfate, filtered and evaporated to give 3.25 g (75%) of 2-carbomethoxy-3-methoxybenzoic acid, mp 140°–141° C. (benzene). Identity was confirmed by mixture mp, co-chromatography and spectroscopic comparison with an authentic sample. ¹H NMR (CDCl₃) δ 3.86 (3H, s, ArCO₂CH₃), 3.93 (3H, s, ArOCH₃), 7.13 (1H, dd, J=8,2 Hz, ArH₄), 7.43 (1H, t, J=8 Hz, ArH₅), 7.68 (1H, dd, J=8,2 Hz, ArH₆, 10.50 (1H, broad s, ArCO₂H); IR (KBr) 3200 (br), 2960, 1740, 1690, 1585, 1475, 1310, 1050 cm$^{-1}$, etc.; mass spectrum m/e (rel. intensity) 211 (m+ +1,5%), 210 M+, 30%), 193 (M+-OH, 2%), 180 (M+-2CH₃, 100%), 179 (M+-OCH₃, 10%), etc.

Anal. for $C_{10}H_{10}O_5$: Calcd.: C, 57.14; H, 4.79. Found: C, 57.07; H, 4.76.

C. Dimethyl 3-methoxyphthalate

An ethereal solution of diazomethane generated from 21.0 g of Diazald was reacted at ice-bath temperature with 14.9 g of 2-carbomethoxy-3-methoxy benzoic acid dissolved in methanol. The excess diazomethane was decomposed with acetic acid after a 15 min. room temperature reaction time. Evaporation of the solvent yielded 15.8 g (100%) of pure ester mp 76°–77° C.; ¹H NMR (CDCl₃), δ 3.80 (3H, s, ArCO₂CH₃), 3.83 (3H, s, ArCO₂CH₃), 3.90 (3H, s, ArOCH₃), 6.97 (1H, dd, J=8,2 Hz, ArH₄), 7.25 (1H, t, J=8 Hz, ArH₅, 7.45 (1H, dd, J=8,2 Hz, ArH₆)a; IR (KBr) 3120, 3040, 2990, 1740, 1595, 1470, 1460, 1440, 1275,a 1205, 1110, 1050 cm$^{-1}$; mass spectrum m/e (rel. intensity) 225 (M+ +1, 3%), 224 (M+, 27%), 194 (M+-2CH₃, 15%), 193 M+-OCH₃, 100%), 165 (M+-CO₂CH₃, 10%), etc.

Anal. for $C_{11}H_{12}O_5$: Calcd.: C, 58.92; H, 5.39. Found: C, 58.85; H, 5.41.

EXAMPLE I

3,4-Dihydro-5,8-dimethoxy-1 (2H)-naphthaleone (1)

This compound was prepared in one step by reacting 1,4-dimethoxybenzene under Friedel-Crafts conditions with γ-butyrolactone. 1,4-Dimethoxybenzene (1.00 g, 7.2 mmol) was suspended in 0.86 g (10 mmol) of γ-butyrolactone. The suspension was cooled in an ice bath and to the cold reaction mixture was added, dropwise, 0.87 ml of trifluoromethanesulfonic acid. The reaction was allowed to proceed under argon at 110°–115° C. for 9.5 hrs. After cooling the solution to room temperature an pouring it into excess ice-cold water, the suspension was extracted with ethyl acetate (3×25 ml). The combined organic layer was washed with cold 5% sodium hydroxide solution (1×20 ml) and water (3×30 ml). The ethyl acetate solution was dried over sodium sulfate and evaporated to yield a dirty brown-colored residue. The latter was subjected to medium pressure column chromatography using hexane:ethyl acetate::7:3 as eluent. Compound (1) was isolated as a light yellow solid (0.75 g, 50% yield): mp 59°–60° C. (from ether-hexane) ¹H NMR (CDCl₃) δ 2.04 (2H, p, ArCH₂CH₂CH₂), 2.66 (2H, t,ArCOCH₂CH₂), 287 (2H, t,ArCH₂CH₂), 3.81 (3H, s, ArOCH₃), 3.85 (3H, s, ArOCH₃), 6.77 (1H, d, J=8 Hz, ArH), 7.00 (1H, d, J=8 Hz, ArH); IR (CDCl₃) 3020, 2970, 2840, 1680, 1590, 1470, 1430, 1265, 1080, 1025 cm$^{-1}$ etc; mass spectrum m/e/ (rel. intensity) 207 (M+ +1, 12%), 206 (M+, 100%), 191 (M+-CH₃, 7%), 178 (M+-CO), 177 (M+-C₂H₅, 78%), 162 (M+-CH₃—CHO, 29%) etc.

Anal. for $C_{12}H_{14}O_3$: Calcd.: C, 69.88; H, 6.84. Found: C, 70.00; H, 6.88.

EXAMPLE 2

A. 7-Bromo-3,4-dihydro-5, 8-dimethoxy-1(2H)naphthaleone (2) (Procedure A)

Tetralone (1) (0.05 g., 0.24 mmol) was dissolved in 2 ml of chloroform. Acetamide (0.10 g) and 0.5 ml of glacial acetic acid were added and the solution was cooled in an ice-bath. The reaction was protected from light by covering the reaction vessel with an aluminum foil. To the stirring cold solution was added 0.05 g (0.29 mmol) of bromine in 0.5 ml of glacial acetic acid. An additional 1 ml of chloroform was added to the stirring solution. The reaction was allowed to continue at 0° C. for 5 hr and at room temperature for 4 hrs. TLC (hexane:ethyl acetate) indicated complete disappearance of the starting material. The excess solvent was removed under a stream of argon and the residue was suspended in water and extracted with chloroform (3×5 ml). The organic layer was dried over sodium sulfate and evaporated to yield a yellow oil. The latter was subjected to medium pressure liquid chromatography using 100% hexane followed by hexane:ethyl acetate::7:3 as eluents. The major product (0.104 g) was identified as the side-chain brominated compound, mp 101°–202° C. (ether) (mp 99°–101° C.); ¹H NMR (CDCl₃) 2.43 (2H, q,ArCH₂CH₂CH), 3.03 (2H, t,ArCH₂CH₂), 3.83 (3H, s, ArOCH₃), 3.86 (3H, s, ArOCH₃), 4.63 (1H, t, CH₂CHBr), 6.81 (1H, d, J=8 Hz, ArH), 7.03 (1H, d, J=8 Hz, ArH). The minor product (0.008 g) was identified as the desired product 2. Two other products were isolated by the above chromatogram, but they were not identified.

B. 7-Bromo-3,4-dihydro-5,8-dimethoxy-1(2H)naphthaleone (2) Procedure B)

Tetralone 1 (14.942 g, 72 mmol), dissolved in 150 ml of dry dimethylformamide, was cooled to ice-bath temperature. Propylene oxide (10.1 ml) followed by a 150 ml diethylformamide solution of N-bromosuccinimide (21.823 g, 0.123 mmol) were slowly added to the cold stirring solution. The reaction flask was equipped with a drying tube and the reaction was allowed to proceed at room temperature for 8 hrs. The solution was then poured into 650 ml of water and the resulting suspension was allowed to stand overnight at room temperature. The product was filtered and dried to yield 15.80 g (76%) of pure monobromo compound mp 82°–83° C. The filtrate was concentrated on a rotary evaporator and extracted with ethyl acetate (3×50 ml), dried over sodium sulfate, and evaporated to yield an additional 2.45 g of Compound (2), mp 82°–83° C. The total weight (18.251 g) of the isolated product represents an 88% yield; $^1$H NMR (CDCl$_3$) δ 2.00 (2H, m J=6 Hz,ArCH$_2$C$\underline{H}_2$CH$_2$), 2.56 (2H, t, J=6 Hz, COC$\underline{H}_2$CH$_2$), 2.86 (2H, t, J=6 Hz,ArC$\underline{H}_2$CH$_2$) 3.80 (6H, s, ArOC$\underline{H}_3$), 7.06 (1H, s, Ar$\underline{H}$); IR (KBr) 2980, 1690, 1565, 1465, 1260, 1210, 1055, etc.; mass spectrum m/e (rel. intensity) 286 (M$^+$+2, 100%), 284 (M$^+$, 98%), 271 (M$^+$+2-CH$_3$, 9%), 269 (M$^+$-CH$_3$, 18%), 258 M$^+$+2-CO, 16%), 256 (M$^+$-CO, 19%), 257 (M$^+$+2-C$_2$H$_5$, 82%), 255 (M$^+$-C$_2$H$_5$, 89%), etc.

Anal. for C$_{12}$H$_{13}$BrO$_3$: Calcd: C, 50.54; H, 4.59. Found: C, 50.56; H, 4.68.

EXAMPLE 3

A.

7-Bromo-1,2,3,4-tetrahydro-5,8-dimethoxy-1-naphthalenol (2A)

Ketone (2) (1.00 g, 0.035 mol) was suspended in 140 ml of isopropanol. The suspension was warmed on a steam bath to make it a homogeneous solution. The latter was cooled to room temperature and charged with sodium borohydride (0.526 g, 0.013 mol). The reaction was allowed to proceed at room temperature under argon, while periodically monitoring by TLC using a 7/3 hexane to ethyl acetate system. At the end of the reaction, the reaction mixture was poured into 500 ml of cold 5% hydrochloric acid solution. The suspension was extracted with ethyl acetate (3×100 ml) and the combined organic layer was washed with brine (1×100 ml) dried over sodium sulfate and evaporated to yield 9.16 g (92%) of oil. The product was found to be analytically pure, hence no further purification was necessary. $^1$H NMR (CDCl$_3$) δ 1.63–2.00 (4H, m,ArCH$_2$C$\underline{H}_2$CH$_2$CH), 2.43–2.59 (2H, m, Ar C$\underline{H}_2$), 2.86 (1H, exchangeable with D$_2$O, m, CHO$\underline{H}$), 3.73 (3H, s, ArOC$\underline{H}_3$), 3.83 (3H, s, ArOC$\underline{H}_3$), 4.90 (1H, m, ArC$\underline{H}$OH), 6.76 (1H, s, Ar$\underline{H}$); IR (CHCl$_3$) 3610 (br), 3025, 2980, 2410, 1575, 1520, 1465, 1420, 1370, 1325, 1210, 1090, 1055, 1035 cm$^-$etc.; mass spectrum m/e (rel. intensity) 288 (M$^+$+2, 94%), 286 (M$^+$, 100%), 270 (M$^+$+2-H$_2$O, 49%), 268 (M$^+$-H$_2$O, 46%), 257 (M$^+$+2-OCH$_3$, 30%), 255 (M$^+$-OCH$_3$, 52%), 193 (M$^+$-Br—CH$_3$, 39%), etc.

Anal. for C$_{12}$H$_{15}$BrO$_3$: Calcd: C, 50.19; H, 5.26. Found: C, 50.13; H, 5.27.

B. 7-Bromo-1,2-dihydro-5,8-dimethoxynaphthalene (2B)

Dehydration was achieved by suspending 2.00 g (7.0 mmol) of alcohol 2A in 50 ml of 15% hydrochloric acid solution. The suspension was heated to 80°–90° C. and stirred vigorously for 6 hrs. The suspension was then cooled to room temperature and extracted with ethyl acetate (3×25 ml). The combined organic layer was washed with saturated sodium bicarbonate (3×25 ml) and water (2×25 ml), dried over sodium sulfate, and evaporated to yield 1.705 g (91%) or pure olefin. mp 110°–111° C.; $^1$H NMR (CDCl$_3$) δ2.16–2.39 (2H,m,ArCH$_2$—C$\underline{H}_2$—CH=CH), 2.53–2.83 (2H, m,ArC$\underline{H}_2$), 2.70 (3H, s, ArOC$\underline{H}_3$), 2.73 (3H, s, ArOC$\underline{H}_3$, 5.96 (1H, dt, J=10 Hz, 4 Hz, ArCH=C$\underline{H}$), 6.60 (1H, dt, J=10 Hz, 4 Hz, 2H, ArC$\underline{H}$=CH$_2$), 6.76 (1H, s, Ar$\underline{H}$); IR (CHCl$_3$) 3010 (sh), 2980, 2950, 2890, 2850, (sh), 1760, 1580, 1465, 1425, 1370, 1330, 1220 (br), 1090, 1065 cm$^{-1}$, etc.; mass spectrum m/e (rel. intensity) 270 (M$^+$+2, 100%), 268 (M$^+$, 100%), 255 (M$^+$+2-CH$_3$, 100%), 253 (M$^+$-CH$_3$, 100%), 174 (M$^+$-CH$_3$—Br, 94%), 158 (M$^+$-OCH$_3$-Br, 99%).

C.

7-Bromo-5,8-dimethoxy-1,2-epoxy-1,2,3,4-tetrahydronaphthalene (2C)

To a solution of Compound 2B (1.161 g, 4.35 mmol) in 25 ml of dry methylene chloride was added, dropwise, a solution of m-chloroperbenzoic acid (80–90%) (1.488 g., 8.62 mmol) in 45 ml of dry methylene chloride. The solution was stirred vigorously while maintained under an atmosphere of argon. After the addition was over, the reaction was allowed to continue at room temperature for two additional hours. The solution was then washed with 20 ml of 1 N sodium hydroxide solution, followed by washing with water (3×20 ml). The organic layer was dried over sodium sulfate and evaporated to yield 1.285 g of product, which contained a small amount of starting material. The crude product was subjected to medium pressure liquid chromatography (hexane:ethyl acetate::7:3) to isolate 0.928 g (76%) of the desired epoxide. A small amount (0.162 g) of unreacted Compound 2 was also recovered. The yield, after taking the recovered starting material into account, is 85%, $^1$H NMR (CDCl$_3$) δ 1.06–2.93 (5H, m,ArCH$_2$C$\underline{H}_2$C$\underline{H}$CH), 3.70 (3H, s, ArOC$\underline{H}_3$), 3.80 (3H, s, ArOC$\underline{H}_3$), 4.16 (1H, d, J = 4 Hz, ArC$\underline{H}$OC$\underline{H}$), 6.80 (1H, s, Ar$\underline{H}$); IR (CHCl$_3$), 3010, 2970, 2860, 2255, 1725, 1570, 1465, 1420, 1380, 1370 (sh), 1330, 1290, 1250 (sh), 1210 (br), 1115, 1080, 1050, 1015 cm$^{-1}$; mass spectrum m/e (rel. intensity) 286 (M$^+$+2, 97%), 284 (M$^+$, 100%), 271 (M$^+$+2-CH$_3$, 27%), 269 (M$^+$-CH$_3$, 27%), 258 (M$^+$+2-CO, 24%), 256 (M$^+$-CO, 33%), 255 (M$^+$+2-OCH$_3$, 33%), 253 (M$^+$-OCH$_3$, 33%), etc.

Anal. for C$_{12}$H$_{13}$BrO$_3$: Calcd: C, 50.54; H, 4.59. Found: C, 50.75; H, 4.69

D.

7-Bromo-3,4-dihydro-5,8-dimethoxy-2(1H)-naphthalenone (3)

To a solution of epoxide (2C) (0.494 g, 1.73 mmol) in 7 ml of chloroform was added 3.5 ml of trifluoroacetic acid. The solution was refluxed for 2 hrs. under argon, and then allowed to stand at room temperature overnight. The solution was once again refluxed for 1 hr. and then allowed to cool to room temperature. Washing the solution with 10 ml of water, drying over sodium sulfate, and evaporating the solvent yielded a yellow oil. Subjecting the product to medium pressure liquid chromatography using hexane-ethyl acetate::7.:3 yielded 0.250 g (51%) of the β-tetralone 44:mp 88°–89° C. $^1$H NMR (CDCl$_3$) δ2.43 (2H, t, J=6 Hz,ArCH$_2$CH$_2$CO), 2.96, (2H, t, J=6 Hz, ArC$\underline{H}_2$CH$_2$), 3.50 (2H, ArC$\underline{H}_2$CO,s), 3.70 (3H, s, ArOC$\underline{H}_3$), 3.73 (3H, s, ArOC$\underline{H}_3$), 6.76 (1H, s, Ar$\underline{H}$); IR (CHCl$_3$) 3030, 2980, 2905, 2840, 2400, 2250, 1780, 1710, 1575, 1510, 1470, 1430, 1400, 1375 (sh), 1335, 1285, 1210 (br), 1170 (sh), 1140, 1080, 1040, 1010 cm$^{-1}$ etc.; mass spectrum m/e/ (rel. intensity) 286 (M$^+$+2, 100%), 284 (M$^+$, 100%), 271 (M$^+$+2-CH$_3$, 25%), 269 (M$^+$-CH$_3$, 25%), 244 (M$^+$+2-CH$_2$=C=O, 31%), 242 (M$^+$-CH$_2$=C=O, 38%), 229 (M$^+$+2,CH$_3$—CH$_2$=C=O, 69%), 277 (M$^+$-CH$_3$-CH$_2$=C=O, 69%), etc.

Satisfactory analysis of this compound could not be obtained because of its tendency to undergo aromatization. Hence, this ketone was converted to its corresponding ethylene ketal, by refluxing the ketone with benzene, ethylene glycol and p-toluenesulfonic acid in a flask equipped with Dean-Stark trap. After work-up, the product obtained was chromatographed by medium pressure liquid chromatography using hexane:ethyl acetate::7:3 as eluent. The product thus obtained was in an oil form which crystallized on standind; mp 74°-76° C.

Anal. for C$_{14}$H$_{17}$BrO$_4$: Calcd: C, 51.08; H, 5.20. Found: C, 51.04; H, 5.09.

EXAMPLE 4

Lithiation of Compound 4 and phthalate conjugation

All the reagents used were pure and perfectly dry. 3-methoxy-dimethyl phthalate was freshly distilled and stored over a 3 molecular sieve. Tetrahydrofuran was freshly distilled over benzophenoneketyl and then securely stored under argon. n-Butyl lithium was quantitated. All the glassware was oven-dried for at least six hours. A reaction flask containing a magnetic stirrer was taken freshly out of the oven and flushed under a high flow of argon. Compound (4) was added to the fairly warm flask and maintained under the argon flow. The flask was closed with the appropriate size rubber septum and tightened by a copper wire .Tetrahydrofuran, withdrawn under positive argon pressure from its container by means of a syringe, was added to the reaction flash containing Compound 4. After dissolving the latter at room temperature, the homogeneous solution was cooled to −80° C. in a dry ice/ether bath. The system was properly insulated and a lapse period of at least 45 minutes was allowed for the homogeneous solution in the flask to equilibrate with the bath temperature. N-butyl lithium, withdrawn under positive pressure of argon by means of a syringe, was added dropwise to the cold ether solution. After TLC indicated that the starting material was completely consumed, dimethyl 3-methoxy phthalate was added at once to the stirring solution. The temperature of the bath was slowly allowed to rise to room temperature and the reaction was quenched by adding a few drops of acetic acid or methanol. After workup, the resulting conjugate and unreacted dimethyl phthalate were the two major products. Minor products, such as dehalogenated compound, were present in traces only.

While the invention has been described in detail and with reference with specific embodiments thereof, it will be apparent to those skilled in the art to which it relates that numerous variations and changes therein are possible without departing from the spirit and scope thereof as defined by the following claims.

What is claimed is:

1. A process for synthesizing asymmetric anthracyclinones which comprises:
    (a) brominating a 5,8-dimethoxy-α-tetralone to yield a 7-bromo-5,8 dimethoxy-α-tetralone as substantially the only isomer,
    (b) transposing the 1-keto group of said 7-bromo-5,8-dimethoxy-α-tetralone to the 2-position to yield the corresponding β-tetralone;
    (c) protecting said transposed keto group,
    (d) lithiating said protected β-tetralone,
    (e) reacting said lithiated compound with a phthalate ester, and
    (f) cyclizing said conjugate to yield an anthracyclinone.

2. The process of claim 1 wherein said brominating step (a) comprises reactng said α-tetralone with a brominating agent in the presence of an HBr scavenger.

3. The process of claim 2 wherein said brominating step (a) comprises reacting said α-tetralone with N-bromosuccinimide in dimethylformamide in the presence of an HBr scavenger.

4. The process of claim 3 wherein said HBr scavenger is propylene oxide.

5. The process of claims 1 or 4 wherein said transposing step (b) is accomplished via formation of the 1,2epoxy derivative of said α-tetralone.

6. The process of claims 1 or 4 wherein phthalate ester is a 3-methoxy phthalate ester.

7. The process of claim 5 wherein said phthalate ester is a 3-methoxy phthalate ester.

8. The process of claims 1 or 4 wherein said cyclizing step (f) comprises reacting said conjugate with trifluoromethane-sulfonic acid.

9. The process of claim 1 which further comprises substituting gem dimethyl groups at the 1-position of said β-tetralone subsequent to step (b).

10. The process of claim 5 which further comprises coupling said anthracyclinone with an amino sugar.

* * * * *